United States Patent [19]

Wood

[11] 4,159,989

[45] Jul. 3, 1979

[54] PROCESS FOR PREPARING ETHYLENE GLYCOL DIACYLATE

[75] Inventor: George R. Wood, Winfield, Ill.

[73] Assignee: Standard Oil Company (Indiana), Chicago, Ill.

[21] Appl. No.: 792,882

[22] Filed: May 2, 1977

[51] Int. Cl.$^2$ .................... C07D 307/32; C07C 69/16
[52] U.S. Cl. .................... 260/343.6; 560/263
[58] Field of Search .................... 560/234, 264, 263; 260/343.6

[56] References Cited

U.S. PATENT DOCUMENTS

| | | | |
|---|---|---|---|
| 3,335,174 | 8/1967 | Norton | 260/497 |
| 3,560,534 | 2/1971 | MacDonald | 260/410.9 |
| 3,562,316 | 2/1971 | Julia | 260/497 |
| 3,668,239 | 6/1972 | Kollar | 260/497 R |
| 3,715,389 | 2/1973 | Hoch | 260/497 R |
| 3,743,672 | 7/1973 | Kollar | 260/497 A |
| 3,770,813 | 11/1973 | Kollar | 260/497 R |
| 3,789,065 | 1/1974 | Kollar | 260/497 R |
| 3,992,417 | 11/1976 | Dessau | 260/343.6 |

OTHER PUBLICATIONS

Dessau; R., et al., *J. Am. Chem. Soc.*, 90, 2706–2707, (1968).
Chemical Abstracts, 65:11405C, (1963), [Lee, J., et al., Tett. Lett., 1962, 1155–1159].
Becker, F. et al., *Organometallic Reactions*, vol. 3, Wiley–Interscience, New York, 1972, pp. 319, 322–323, 328–329.
Organometal. Chem. Rev., 3, 63, (1968).
Chatt, J., Chem. Rev., 48, 7, (1951).

*Primary Examiner*—John M. Ford
*Assistant Examiner*—Richard A. Schwartz
*Attorney, Agent, or Firm*—William H. Magidson; Arthur G. Gilkes; William T. McClain

[57] ABSTRACT

Production of ethylene glycol diacylate by reacting ethylene, divalent mercury compound and an aliphatic acid to produce an acyloxyethylmercuric acylate and disproportionating said acyloxyethylmercuric acylate by heating in the presence of a catalytic concentration of perchloric acid to form an ethylene glycol diacylate and lactone. When the acyloxyethylmercuric acylate is acyloxyethylmercuric acetate, the disproportionation produces gamma-butyrolactone as the lactone.

9 Claims, No Drawings

PROCESS FOR PREPARING ETHYLENE GLYCOL DIACYLATE

This invention relates to the production of ethylene glycol diesters wherein an acyloxyethylmercuric acylate is disproportionated to ethylene glycol diester in the presence of a perchloric acid catalyst.

Ethylene glycol and butylene glycol are useful in the production of polyesters. These monomers can be produced by various techniques, such as the hydrolysis of glycol esters in the case of ethylene glycol or reduction of gamma butyrolactone in the case of butylene glycol. Various gamma substituted butyrolactones have been produced by reacting an olefin containing three or more carbon atoms with acetic acid in the presence of catalysts such as lead tetraacetate, etc. See, for example, Dessau U.S. Pat. No. 3,992,417, Journal of the American Chemical Society, Volume 90, starting at pages 2706, 5903, and 5905 (1968). Apparently all of these reactions result in the formation of a substituent at the gamma position of the gamma-butyrolactone.

The general object of this invention is to provide a method of producing glycol esters or mixtures of glycol esters and unsubstituted gamma butyrolactone. Another object of this invention is to provide a method of producing glycol esters or mixtures of glycol esters and unsubstituted gamma butyrolactones from ethylene. Other objects appear hereinafter.

I have now found that it is possible to produce ethylene glycol diacylates from ethylene by reacting ethylene in an aliphatic carboxylic acid medium using a mercuric catalyst, such as mercuric acetate, to produce acyloxyethylmercuric acylates and that the acyloxyethylmercuric acylates can be disproportionated to form unsubstituted ethylene glycol diacylate and mixtures of ethylene glycol diacylate and lactones using a perchloric acid catalyst. In those cases where the aliphatic carboxylic acid is acetic acid, gamma-butyrolactone is produced. In simplified form, the reactions can be represented as follows, when Ac is acetic acid:

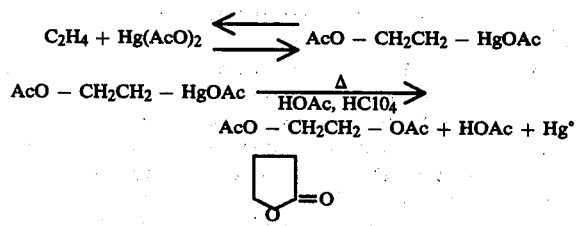

The acyloxyethylmercuric acylate can be rapidly and quantitatively formed by contacting a mercuric salt, preferably a mercuric acylate, with ethylene in an aliphatic carboxylic acid at ambient temperature (0° to 40° C.). By raising the temperature of the acyloxyethylmercuric acylate in the presence of perchloric acid, the desired conversion or disproportionation to lactone and ethylene glycol diacylate takes place. In general, the higher the concentration of perchloric acid the higher the concentration of glycol esters formed. In the absence of perchloric acid there is relatively little conversion to the desired products. In those cases where only ethylene glycol diacylate is desired, the disproportionation can be carried out in the presence of excess water.

The aliphatic acids useful in this invention contain 2 to 8 carbon atoms, such as acetic acid, propionic acid, butyric acid, n-pentanoic acid, n-hexanoic acid, n-heptanoic acid, n-octanoic acid, 2-ethylhexanoic acid, etc. One or more aliphatic acids can be used as the reaction medium. Acetic acid is preferred since the disproportionation of acetoxyethylmercuric acetate produces unsubstituted gamma-butyrolactone and ethylene glycol diacetate. It is believed that the higher acids containing 3 to 8 carbon atoms would produce glycol diester and alpha substituted butyrolactones on disproportionation.

The mercuric compounds useful in this invention are preferably soluble in the aliphatic acid and can include mercuric salts of aliphatic acids containing 1 to 8 carbon atoms, mercuric halides (e.g. bromides, chlorides, etc.), mercuric oxide, mercuric nitrate, etc.

The perchloric acid can be used in a concentration of about 0.0001 to 0.5 moles per mole of divalent mercury or acyloxyethylmercuric acylate. In general, as the concentration of perchloric acid increases, the percent of acyloxyethylmercuric acylate disproportionating increases and the greater the ratio of glycol diester to lactone. The lower the concentration of perchloric acid, the higher the ratio of lactone to glycol diester.

In somewhat greater detail, the acyloxyethylmercuric acylate can be formed by adding ethylene to a reaction medium containing a mercuric compound dissolved in an aliphatic acid. If desired, the perchloric acid catalyst for the disproportionation reaction can be present during the addition of ethylene. The reaction can be carried out at ambient conditions (0° to 40° C.) and at a pressure of one or more atmospheres. The acyloxyethylmercuric acylate is then heated to 100° to 250° C., preferably 125° to 200° C. while maintaining an ethylene partial pressure of one or more atmospheres in the presence of perchloric acid to disproportionate into ethylene glycol diacylate and lactone. It is preferred to carry out the disproportionation under substantially anhydrous conditions (i.e. any water present is due to the water in the perchloric acid or minor amounts in the aliphatic acid) when a mixture of ethylene glycol diacylate and lactone is desired. Higher concentrations of water can be used to produce substantially only the ethylene glycol diacylate.

In a preferred method of carrying out a batch reaction utilizing acetic acid as a solvent and mercuric acetate as the divalent mercuric compound, ethylene is pressurized into the reactor containing an acetic acid solution of mercuric acetate and a catalytic amount of perchloric acid. At ambient temperature and pressure there is rapid formation of acyloxyethylmercuric acetate. On completion of the addition of ethylene, the temperature of the reactor is raised and the partial pressure of ethylene is permitted to develop to over 1 atmosphere. After the completion of the disproportionation reaction, the reactor contents are removed and the effluent ethylene glycol diacetate and gamma butyrolactone are recovered by fractional distillation. The remainder of the effluent containing unreacted mercuric compounds, mercurous salts, elemental mercury and acid catalyst can be oxidized to convert all the mercury to the divalent acid form.

In a continuous process the reactor can be maintained at a somewhat higher temperature and pressure with the continuous addition of ethylene, acetic acid and mercuric compound.

EXAMPLES I TO IX

A one liter titanium autoclave equipped with a magnetically driven agitator dip-leg, thermocouple, vent and knock-back condensor with trap, containing about 500 grams glacial acetic acid, 95 grams mercuric acetate and the concentration of 70% aqueous perchloric acid indicated in Table I at 25° C. was purged with nitrogen. Unless indicated in the discussion following the Tables, the only water present during the reaction was from the perchloric acid. Ethylene was added through the dip-leg at a rate of about 1.9 moles per hour with vigorous agitation. After about ten minutes, the slightly exothermic reaction temperature had risen to about 28° to 30° C. and the reaction ceased, as evidenced by no further ethylene absorption and cooling of the reactants. The autoclave was then sealed and heated to about 150° to 175° C. with the pressure permitted to rise due to the increased vapor pressure of acetic acid and to freed ethylene from the mercury/ethylene adduct for about 45 or 90 minutes. The autoclave was cooled and the product filtered. The liquid phase was analyzed by gas chromatography and mass spectroscopy. The results are set forth in Table I and Table II below.

Table I

| Example | Time in (Minutes) | Temp. in (°C.) | Max. Pressure (Psig) | mmole per gram reactants | | Mole % Yield on Hg++ | |
|---|---|---|---|---|---|---|---|
| | | | | HClO$_4$ | H$_2$O | Diacetate | Lactone |
| I | 90 | 150 | 53 | .050 | .117 | 44.0 | 1.0 |
| II | 90 | 150 | 66 | .050 | .117 | 48.6 | 2.1 |
| III | 90 | 150 | 68 | .006 | .014 | 3.8 | 8.9 |
| IV | 90 | 150 | 68 | 0 | 0 | 0.1 | 0.6 |
| V | 90 | 175 | 117 | .006 | .014 | 23.9 | 23.8 |
| VI | 90 | 150 | 82 | .0015 | .003 | 0.7 | 4.7 |
| VII | 90 | 150 | 89 | .005 | 2.33 | 1.9 | 0.0 |
| VIII | 45 | 175 | 106 | .006 | 0 | 19.4 | 15.0 |
| IX | 90 | 175 | 106 | .006 | 0 | 25.1 | 15.9 |

Table II

Effect of Perchloric Acid Concentration on Product Distribution After 90 Minutes at 150° C.

| mm HClO$_4$ per gram reactant | Moles Lactone per Moles Diacetate | Total Mole % Yield of Products Based on Moles Hg++ |
|---|---|---|
| 0 | 6 | .7 |
| .0015 | 6.7 | 5.4 |
| .006 | 2.3 | 12.7 |
| .05 | .034 | 47.9 |

Tables I and II show that the distribution of products is very dependent on the amount of perchloric acid present. At higher perchloric acid concentration the diacetate is the favored product while at low concentrations the lactone is favored. A similar correlation can also be made between the product ratio and the amount of water present in these runs. This is because the water present was due to the addition of aqueous perchloric acid and the water's concentration therefore changed proportionately with that of the perchloric acid. The water's influence can be independently assessed, however, by comparison of Example V with Examples VIII and IX. These were identical experiments except that in Examples VIII and IX a stoichiometric amount of acetic anhydride was added to consume the water. This elimination of the water resulted in a slight decrease of the lactone to diacetate ratio whereas, as shown in Table II, a reduction in both water and perchloric acid results in an increase in the ratio. Thus, for the concentration range employed here, it is the perchloric acid that dominates the product distribution. While small amounts of water do not greatly influence the reaction, an excess amount, such as that used in Example VII, greatly inhibits the overall reaction rate and virtually eliminates the formation of gamma-butyrolactone.

Both the reaction rate and product distribution are affected by the reaction temperature which is evident by comparing Examples III and V in Table I. All conditions were the same in these Examples except for a 25° C. difference in temperature. The higher temperature resulted in a faster conversion rate (47.7 moles % vs. 12.7 mole % yields after 90 minutes) and in a greater diacetate selectivity (1.0 vs. 2.3 lactone to diacetate mole ratio).

I claim:

1. The process of disproportionating an acyloxyethylmercuric acylate to ethylene glycol diacylate which comprises heating a composition consisting essentially of an aliphatic carboxylic acid and an acyloxyethylmercuric acylate with a catalytic concentration of perchloric acid.

2. The process of claim 1, wherein the acyloxyethylmercuric acylate is acetoxyethylmercuric acetate.

3. The process of claim 2, wherein the aliphatic carboxylic acid comprises an acetic acid solvent.

4. The process of claim 3, wherein the perchloric acid comprises 0.0001 to 0.5 mole per mole of acetoxyethylmercuric acetate.

5. The process of claim 4, wherein the composition is substantially anhydrous and a mixture of glycol diacylate and gamma-butyrolactone is produced.

6. The process of producing ethylene glycol diacylate which comprises the steps of reacting ethylene, a divalent mercury compound and an aliphatic acid to produce an acyloxyethylmercuric acylate and disproportionating said acyloxyethylmercuric acylate by heating in the presence of a catalytic concentration of perchloric acid to form an ethylene glycol diacylate.

7. The process of claim 6, wherein perchloric acid is present during the reaction of ethylene, divalent mercury compound and aliphatic acid in a concentration of 0.0001 to 0.5 mole per mole of divalent mercury compound.

8. The process of claim 6, wherein the aliphatic acid comprises acetic acid.

9. The process of claim 8, wherein the process is carried out under substantially anhydrous conditions and a mixture of glycol diacylate and gamma-butyrolactone is produced.

* * * * *